(12) United States Patent
Golenhofen

(10) Patent No.: US 7,991,109 B2
(45) Date of Patent: Aug. 2, 2011

(54) X-RAY MULTICHANNEL SPECTROMETER

(75) Inventor: Rainer Golenhofen, Ettlingen (DE)

(73) Assignee: Bruker AXS GmbH, Karlsruhe (DE)

( * ) Notice: Subject to any disclaimer, the term of this patent is extended or adjusted under 35 U.S.C. 154(b) by 50 days.

(21) Appl. No.: 12/656,345

(22) Filed: Jan. 27, 2010

(65) Prior Publication Data

US 2010/0195795 A1 Aug. 5, 2010

(30) Foreign Application Priority Data

Jan. 31, 2009 (DE) .......................... 10 2009 006 984

(51) Int. Cl.
*G01N 23/223* (2006.01)

(52) U.S. Cl. ........................................... 378/46; 378/71

(58) Field of Classification Search .............. 378/44–50, 378/70–90, 147, 152
See application file for complete search history.

(56) References Cited

U.S. PATENT DOCUMENTS

| 4,852,135 A | 7/1989 | Anisovich |
| 5,406,608 A | 4/1995 | Yellepeddi |
| 2006/0133570 A1 | 6/2006 | Mazor |

FOREIGN PATENT DOCUMENTS

| DE | 1 100 299 | 9/1961 |
| DE | 1 498 739 | 11/1968 |
| DE | 1 498 740 | 11/1968 |
| DE | 1 498 741 | 11/1968 |
| DE | 100 65 277 | 12/2001 |

*Primary Examiner* — Courtney Thomas
(74) *Attorney, Agent, or Firm* — Paul Vincent

(57) ABSTRACT

An X-ray multichannel spectrometer comprising a polychromatic source (2), a holding means (3) for holding a sample (1), a fluorescence channel (4) that selects X-ray beams of a special wavelength and energy, and a detector (5) for measuring the selected X-ray beams, a diffractometry channel (6) that selects, by means of a monochromator (7), an X-ray beam wavelength of the source subsequent to diffraction of the X-ray beams by the sample, and a detector (8) for measuring the selected X-ray beams, is characterized in that a single slit device (9) is provided between the source and the sample, which can be moved transversely with respect to the direction of the beam from the source, and the monochromator of the diffractometry channel is stationarily disposed with respect to the source and the sample and has an entry single slit (10) which defines, together with the movable single slit device and the sample position, the characteristic diffraction angle 2θ of a predetermined crystal structure of the polycrystalline sample at the wavelength of the source selected by the monochromator. In this fashion, reliable element analysis and inexpensive X-ray diffraction can be performed with the same device, wherein the at least three collimator arrangements that have been necessary up to now for the diffractometry channel, are omitted and the monochromator does not require any complex diffraction mechanism in the diffractometry channel.

16 Claims, 4 Drawing Sheets

X-RAY MULTICHANNEL SPECTROMETER

This application claims Paris Convention priority of DE 10 2009 006 984.4 filed Jan. 31, 2009 the complete disclosure of which is hereby incorporated by reference.

BACKGROUND OF THE INVENTION

The invention concerns an X-ray spectrometer for carrying out both an element analysis and a structural analysis of a polycrystalline sample with
 a) a polychromatic source for providing an X-ray beam that is incident on the sample,
 b) a holding means for holding the sample,
 c) one or more fluorescence channels which can select X-ray beams of a special wavelength and energy and have detectors for measuring the selected X-ray beams,
 d) at least one diffractometry channel which is configured such that it selects, by means of a monochromator, an X-ray beam wavelength of the source subsequent to diffraction of the X-ray beams by the sample, and has a detector for measuring the selected X-ray beams.

An X-ray multichannel spectrometer of this type is disclosed in U.S. Pat. No. 5,406,608A.

The X-ray multichannel spectrometer described in U.S. Pat. No. 5,406,608A moreover also has a diffractometry channel for X-ray structural analysis, which is operated with parallel beam optics, in addition to the conventional fluorescence channels which measure the emitted X-ray fluorescence radiation that is characteristic for a certain material in each case and from which the presence and, if necessary, the relative amount of certain elements in the measuring sample can be concluded. In the conventional X-ray spectrometer, a first collimator arrangement must initially be placed or inserted between the X-ray source and the sample to be measured in order to use this diffractometry channel for measurements. The diffractometry channel moreover contains a monochromator which can be rotated with respect to the sample and has a second collimator arrangement at its entry, through which the X-ray radiation that is diffracted by the sample at a certain angle is incident on a crystal, where it is also diffracted and is incident on a detector via a third collimator arrangement.

The conventional X-ray multichannel spectrometer is disadvantageous due to high construction expenses and the corresponding susceptibility to disturbances as well as high production costs. The parallel beam optics that is used for the diffraction analysis moreover requires a large amount of space, since the collimators have considerable depth. There must be an adequate amount of space for the first collimator arrangement between the source and the sample. This space also remains during fluorescence measurements, in which the first collimator arrangement is removed from the area between the source and the sample, and therefore causes permanent strong reduction of the beam intensity.

In the conventional X-ray multichannel spectrometer, the entire monochromator is moved in a curved, usually circular, motion about the sample center to perform a diffraction scan. The mechanism that is required for this purpose is also very complex and also requires a great deal of space, maintenance and expense.

In contrast thereto, it is the object of the invention to modify a conventional X-ray multichannel spectrometer of the above-mentioned type with simple technical means in such a fashion that one and the same device enables reliable element analysis and inexpensive X-ray diffraction, wherein the at least three collimator arrangements for the diffractometry channel, which are required according to prior art, are omitted and the diffraction scan can be performed without complex motion mechanism of the monochromator in the diffractometry channel.

SUMMARY OF THE INVENTION

This object is achieved in accordance with the invention in a surprisingly simple but effective fashion in that a single slit device is provided between the source and the sample, which can be moved transversely with respect to the direction of the beam from the source, and the monochromator of the diffractometry channel is disposed in a stationary fashion with respect to the source and the sample and has an entry single slit that defines, together with the movable single slit device and the sample position, the characteristic diffraction angle $2\theta$ of a predetermined crystal structure of the polycrystalline sample at the wavelength of the source selected by the monochromator.

The simple and inexpensive single slit device of the present invention, which replaces the considerably more complex first collimator arrangement of the conventional X-ray multichannel spectrometer, requires only very little space, since, in practice, the slit has a depth of only approximately 2 mm.

The compact Bragg-Brentano optical path of the inventive X-ray multichannel spectrometer moreover achieves a much larger $2\theta$ diffraction angle (larger than 146°) in contrast to the conventional parallel optical path. In the particularly important case of application of free lime (CaO) for example, the diffraction angle can therefore be measured with the Rhodium-L$\alpha$ line which is approximately 7 times more intense than the Rhodium-L$\beta$ line.

In contrast to the complex curved pivoting motion of the entire monochromator and introduction of the first collimator arrangement into the space between the source and the sample for recording a diffraction scan in an X-ray spectrometer of the type described in U.S. Pat. No. 5,406,608A, the inventive X-ray multichannel spectrometer provides very easy handling by simply introducing the single slit device between the source and the sample, which requires only minimum mechanical means. The movement of the monochromator in the diffractometry channel is completely omitted.

In a particularly preferred embodiment of the inventive X-ray spectrometer, the movable single slit device can be moved into several positions, preferably in a continuous fashion, in particular in a linear fashion. The single slit device of very simple spectrometers may also be constructed in such a fashion that it can be removed or at least be sufficiently pivoted out of the optical path of the X-ray source in order to enable a measuring mode with one of the fluorescence channels.

In simple and particularly inexpensive embodiments of the inventive X-ray spectrometer, the movable single slit device is formed from two collimator blades.

In particularly advantageous embodiments of the invention, the slit openings of the single slit device and the entry single slit are adjusted to the half-width of the measured selected X-ray radiation. In this fashion, the arrangement can be optimally adjusted to the properties of the crystallites in the measuring sample.

In many practical applications of the inventive X-ray multichannel spectrometer, the X-ray source has a Rhodium anode, since the Rhodium-K and Rhodium-L lines excite a large element range and the conventional X-ray tube windows have a transmission intensity of 70% for the radiation of Rhodium-L$\alpha$ lines.

In many particularly important applications, the predetermined crystal structure of the polycrystalline sample will be that of CaO (free lime). A considerable part of the X-ray multichannel spectrometers of this type are currently used worldwide exactly for this analysis range.

Embodiments of the inventive X-ray multichannel spectrometer, in which the characteristic diffraction angle 2θ is larger than 140°, preferably 2θ=146°, are favorable exactly for free lime applications of this type.

In embodiments of the invention, in which the single slit device, the sample and the entry single slit of the monochromator are disposed on a Rowland circle, one can operate with a beam opening angle of 10° without substantially interfering with the resolution. The conventional collimator, however, must always have a maximum divergence of approximately 1°. For this reason, in an inventive X-ray multichannel spectrometer, the Bragg condition for 2θ can be met even when the X-ray radiation strongly diverges and the monochromator has a relatively large opening angle, which yields substantial gain in useful radiation intensity.

Advantageous embodiments of the invention also achieve a high intensity yield, in which the monochromator of the diffractometry channel is provided with a curved focusing crystal.

In preferred further developments of these embodiments, the focusing crystal has a logarithmic curvature. This shape is a good compromise between the particularly high resolution of a (very expensive) Johansson crystal (exact focusing) and the Johann crystal that can be produced at substantially reduced costs.

In practice, the wavelength selected by the monochromator in the diffractometry channel of most inventive X-ray multichannel spectrometers will be equal to a characteristic wavelength of the source. Use of X-ray bremsstrahlung is also possible.

The focusing monochromator in the diffractometry channel of an inventive X-ray multichannel spectrometer may also be a monochromator having almost the same construction as those used for the fluorescence channels. This considerably reduces the production and operating costs of the spectrometer, since the number of different components that are used and must be maintained are considerably reduced compared e.g. to prior art.

The invention also concerns a method for operating an inventive X-ray spectrometer, which is characterized in that, during measurement of the selected X-ray radiation, the single slit device is moved over several measuring positions (scan). A scan of this type may also be used to determine the optimum diffraction angle 2θ and adjust the apparatus accordingly. It is e.g. also possible to record an integral of the measured intensity under a desired diffraction line.

Further advantages of the invention can be extracted from the description and the drawing. The features mentioned above and below may be used individually or collectively in arbitrary combinations. The embodiments shown and described are not to be understood as exhaustive enumeration but have exemplary character for describing the invention.

DESCRIPTION OF THE PREFERRED EMBODIMENT

Figure 1:
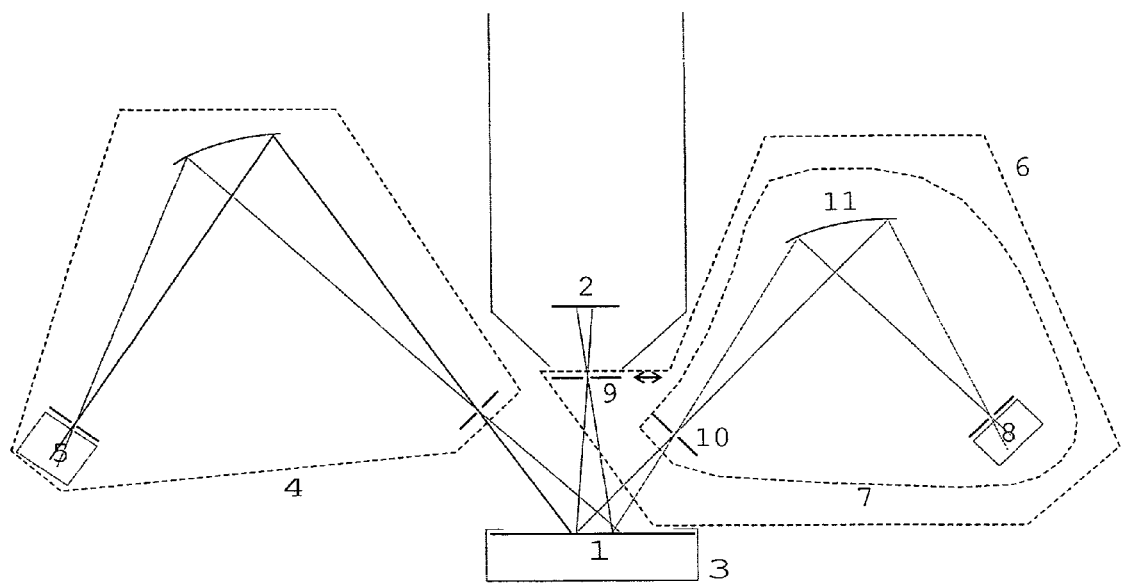
FIG. 1 shows a schematic sectional view of an embodiment of the inventive X-ray multichannel spectrometer with movable single slit device between the source and the sample without collimator arrangements.

The highly schematic sectional view of FIG. 1 shows an embodiment of an inventive X-ray spectrometer for carrying out both an element analysis and a structural analysis of a polycrystalline sample 1.

A polychromatic source 2, which preferably has a Rhodium anode, is used to provide an X-ray beam that is incident on the sample 1. The sample 1 is held by a holding means 3.

On the left-hand side of the source 2 in the drawing, only one fluorescence channel 4 of several feasible fluorescence channels is shown, which can select X-ray beams of a special wavelength and energy and each comprises a respective detector 5 for measuring the selected X-ray beams.

On the right-hand side of the source, one diffractometry channel 6 of several feasible channels is shown, which is configured such that it selects, by means of a monochromator 7, an X-ray wavelength of the source 2 subsequent to diffraction of the X-ray beams by the sample 1. The diffractometry channel 6 also has a detector 8 for measuring the selected X-ray beams.

One particular feature of the inventive X-ray multichannel spectrometer consists in that a single slit device 9 is provided between the source 2 and the sample 1, which can be moved transversely with respect to the direction of the beam from the source 2 and which can preferably be displaced, in a continuous, in particular, linear fashion, as indicated by the double arrow in FIG. 1.

The monochromator 7 of the diffractometry channel 6 is stationarily mounted with respect to the source 2 and the sample 1 and has an entry single slit 10 that defines, together with the movable single slit device 9 and the sample position, the characteristic diffraction angle 2θ of a predetermined crystal structure of the polycrystalline sample 1 at the wavelength of the source 2 that is selected by the monochromator 7. The selected wavelength of the monochromator 7 can be selected like a characteristic wavelength of the source 2.

As indicated in FIG. 1, the monochromator 7 of the diffractometry channel 6 has a curved focusing crystal 11 with a preferably logarithmic curvature.

One particular advantage of the inventive X-ray multichannel spectrometer consists in that the fluorescence channels 4 may be constructed from the same components as the monochromator 7 of the diffractometry channel 6.

Figure 2:
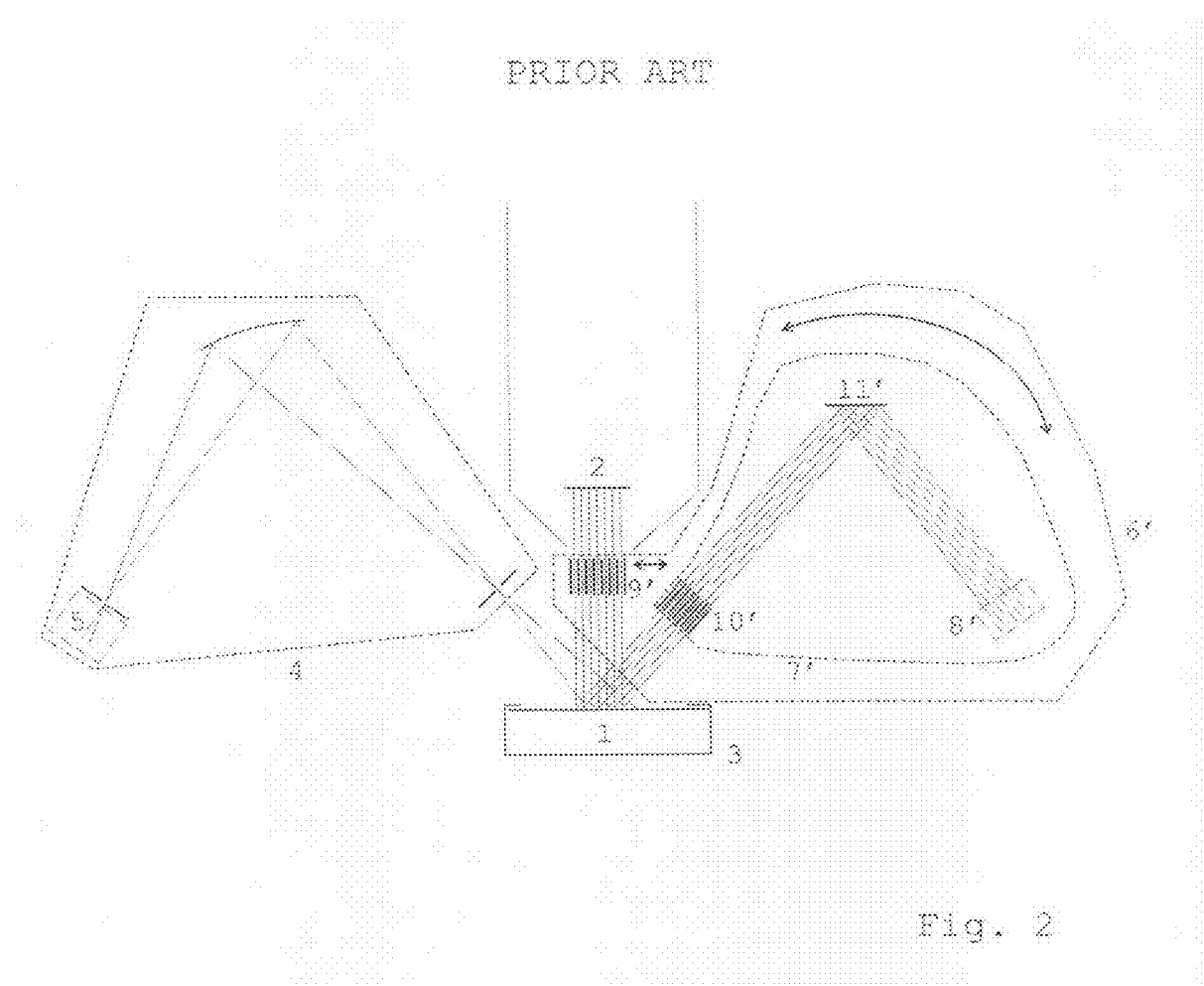
FIG. 2 shows an X-ray multichannel spectrometer according to prior art with collimator arrangements in the diffractometry channel.

FIG. 2 schematically shows an X-ray multichannel spectrometer according to the above-discussed prior art. While the source 2 and the fluorescence channels 4 have a similar design as in the inventive spectrometer of FIG. 1, the diffractometry channel 6' of the conventional spectrometer differs in that voluminous collimator arrangements of a considerably more complex construction are used in this case instead of simple single slits 9, 10, i.e. a first collimator arrangement 9' which can be introduced into the area between the source 2 and the sample 1, a second collimator arrangement 10' at the entry of the monochromator 7', and a third collimator arrangement 8' with detector. The monochromator 7' utilizes an X-ray mirror 11' instead of a curved focusing crystal.

The monochromator 7' of the conventional apparatus must additionally also be movable along an arc for recording a diffraction scan in the diffractometry channel 6', which is indicated in FIG. 2 with a curved double arrow. In the inventive apparatus according to FIG. 1, merely the single slit device 9 is moved over several measuring positions during the measurement of the selected X-ray radiation, while the monochromator 7 remains stationary.

Figure 3:
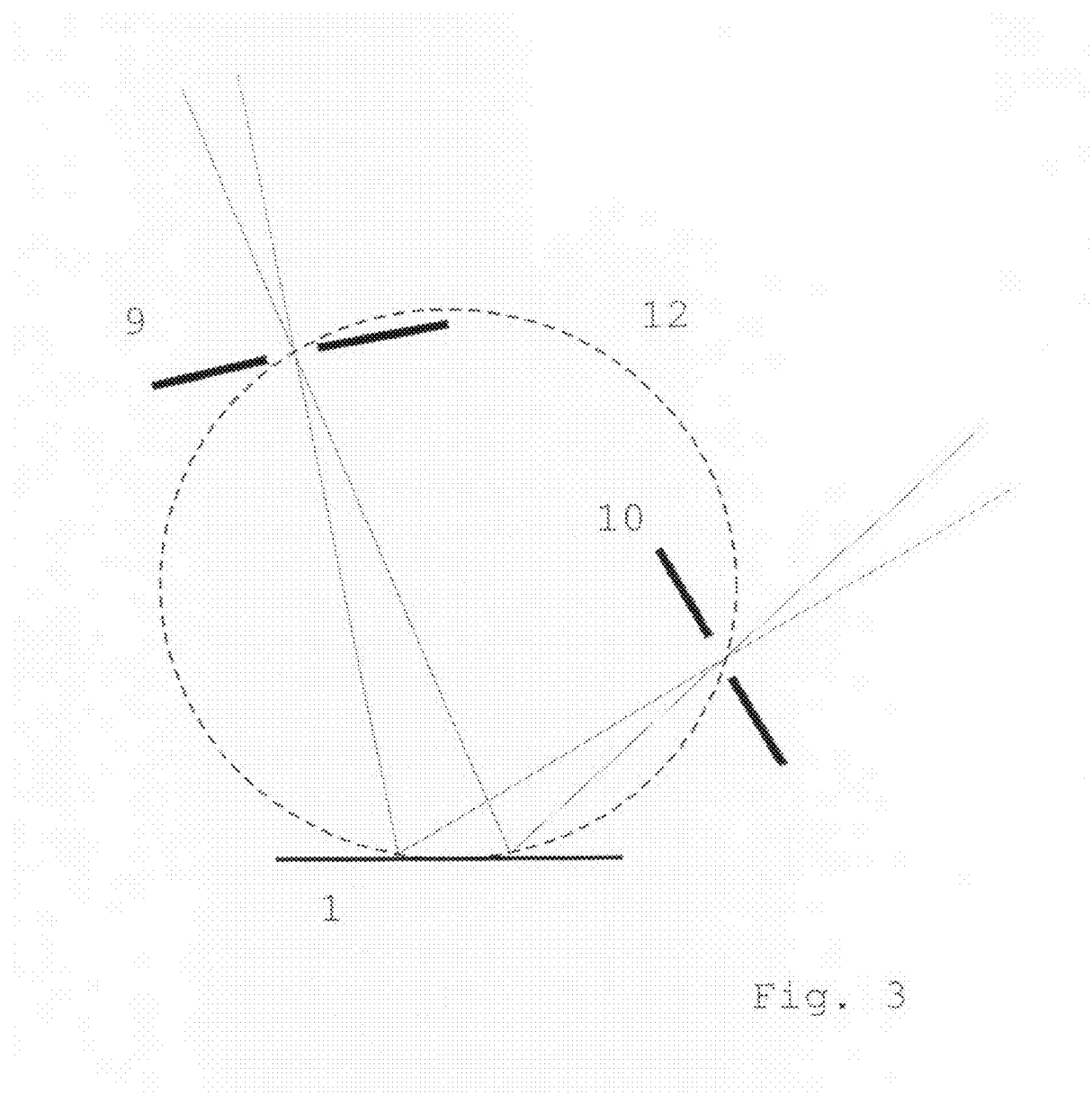
FIG. 3 shows a schematic detailed view of an inventive diffractometer, in which the single slit device, the sample and the entry single slit of the monochromator are disposed on a Rowland circle.

FIG. 3 schematically shows, in greater detail, an embodiment of the inventive X-ray multichannel spectrometer, in which the single slit device 9, the sample 1, and the entry single slit 10 of the monochromator are disposed on a Rowland circle 12.

Figure 4:
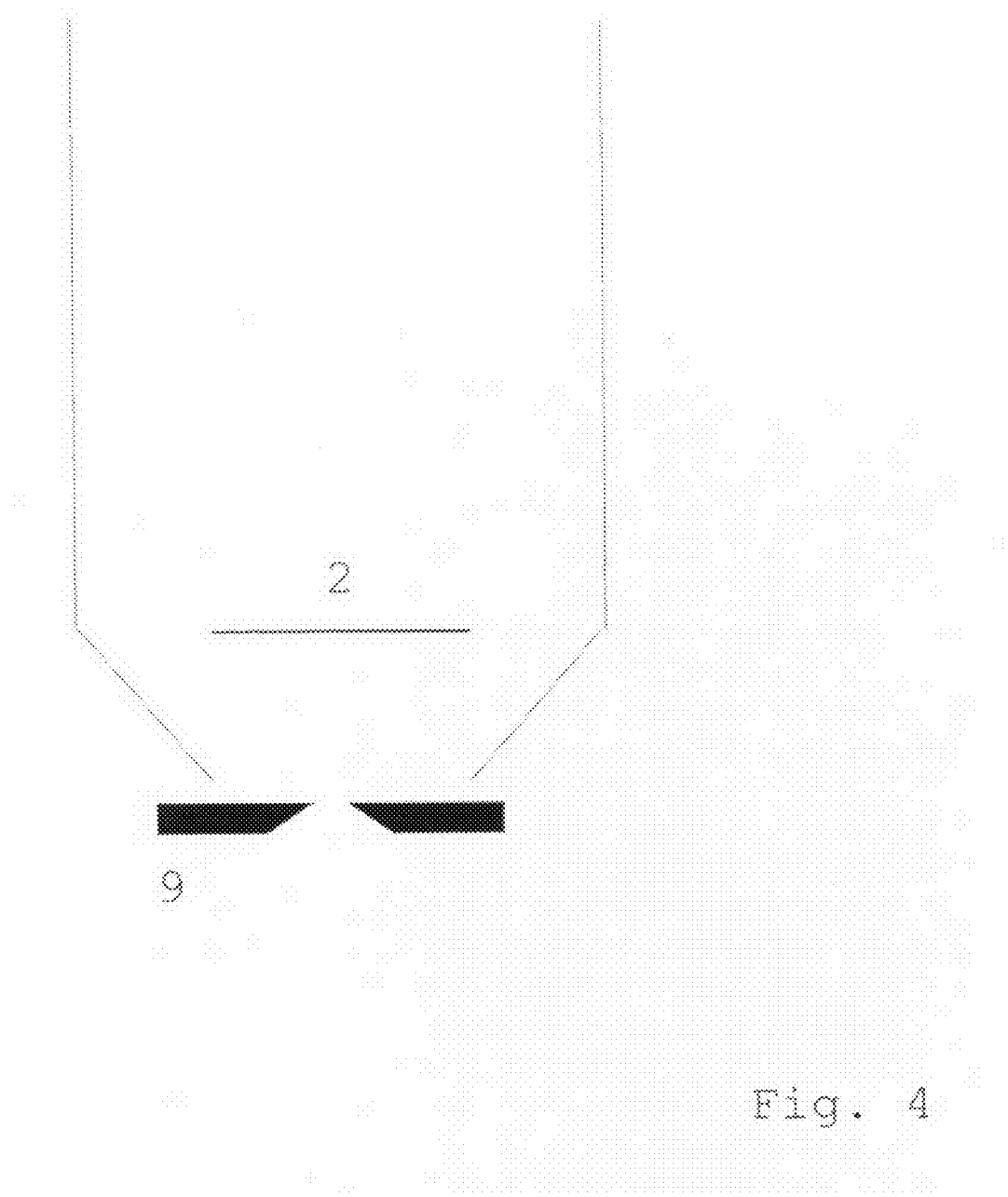
FIG. 4 shows a schematic sectional view of an X-ray source with upstream single slit device formed from two collimator blades in an inventive X-ray multichannel spectrometer.

FIG. 4 shows a movable single slit device 9 disposed at the outlet of the X-ray source 2, which is formed from two collimator blades.

LIST OF REFERENCE NUMERALS 1 sample
2 source
3 holding means
4 fluorescence channel
5 detector
6 diffractometry channel
6' conventional diffractometry channel
7 monochromator
7' conventional monochromator
8 detector with single slit
8' conventional detector with collimator
9 single slit device
9' conventional first collimator arrangement
10 entry single slit
10' conventional second collimator arrangement
11 curved focusing crystal
11' X-ray mirror
12 Rowland circle

I claim:

1. An X-ray spectrometer for carrying out both an element analysis and a structural analysis of a polycrystalline sample disposed at a sample position, the spectrometer comprising:
   a polychromatic source for providing an X-ray beam that is incident on the sample;
   a holder for holding the sample;
   one or more fluorescence channels which can select X-ray beams of a particular wavelength and energy and which have detectors for measuring selected X-ray beams;
   at least one diffractometry channel which is configured to select, by means of a monochromator, an X-ray beam wavelength of said source subsequent to diffraction of said X-ray beam by the sample and having a detector for measuring said selected X-ray beams; and
   a moveable single slit device disposed between the source and the sample for transverse motion relative to a direction of said X-ray beam from said source, wherein said monochromator of said diffractometry channel is stationarily disposed with respect to said source and the sample and has an entry single slit which defines, together with said movable single slit device and the sample position, a characteristic diffraction angle $2\theta$ of a predetermined crystal structure of the polycrystalline sample at a wavelength of said source selected by said monochromator.

2. The X-ray spectrometer of claim 1, wherein said movable single slit device can be moved to several positions.

3. The X-ray spectrometer of claim 2, wherein said movable single slit device can be moved in a continuous fashion.

4. The X-ray spectrometer of claim 2, wherein said movable single slit device can be moved in a linear fashion.

5. The X-ray spectrometer of claim 1, wherein said movable single slit device is formed from two collimator blades.

6. The X-ray spectrometer of claim 1, wherein slit openings of said single slit device and of said entry single slit are adjusted to a half width of a measured selected X-ray radiation.

7. The X-ray spectrometer of claim 1, wherein said source has a Rhodium anode.

8. The X-ray spectrometer of claim 1, wherein a predetermined crystal structure of the polycrystalline sample is that of CaO (free lime).

9. The X-ray spectrometer of claim 1, wherein said characteristic diffraction angle $2\theta > 140°$.

10. The X-ray spectrometer of claim 9, wherein $2\theta \approx 146°$.

11. The X-ray spectrometer of claim 1, wherein said single slit device, the sample and said entry single slit of said monochromator are disposed on a Rowland circle.

12. The X-ray spectrometer of claim 1, wherein said monochromator has a curved focusing crystal.

13. The X-ray spectrometer of claim 12, wherein said focusing crystal has a logarithmic curvature.

14. The X-ray spectrometer of claim 1, wherein said selected wavelength of said monochromator is equal to a characteristic wavelength of said source.

15. The X-ray spectrometer of claim 1, wherein said fluorescence channels are formed from same components as said monochromator of said diffractometry channel.

16. A method for operating the X-ray spectrometer of claim 1, the method comprising the step of moving said single slit device over several measuring positions during a measurement scan.

* * * * *